(12) United States Patent
Lueke

(10) Patent No.: US 9,889,873 B2
(45) Date of Patent: Feb. 13, 2018

(54) METHOD AND DEVICE FOR AN AUTOMATIC STEERING INTERVENTION

(71) Applicant: Continental Teves AG & Co. oHG, Frankfurt (DE)

(72) Inventor: Stefan Lueke, Rosbach vor der Hoehe (DE)

(73) Assignee: Continental Teves AG & Co. oHG, Frankfurt (DE)

( * ) Notice: Subject to any disclaimer, the term of this patent is extended or adjusted under 35 U.S.C. 154(b) by 0 days.

(21) Appl. No.: 14/913,080

(22) PCT Filed: Sep. 10, 2014

(86) PCT No.: PCT/DE2014/200465
§ 371 (c)(1),
(2) Date: Feb. 19, 2016

(87) PCT Pub. No.: WO2015/048959
PCT Pub. Date: Apr. 9, 2015

(65) Prior Publication Data
US 2016/0200348 A1    Jul. 14, 2016

(30) Foreign Application Priority Data

Oct. 1, 2013  (DE) .................. 10 2013 219 867

(51) Int. Cl.
*A61B 5/11* (2006.01)
*B62D 1/04* (2006.01)
(Continued)

(52) U.S. Cl.
CPC ............ *B62D 1/046* (2013.01); *A61B 5/1125* (2013.01); *A61B 5/6893* (2013.01); *B62D 5/003* (2013.01);
(Continued)

(58) Field of Classification Search
USPC .............................. 701/2, 42, 48, 41; 74/552
See application file for complete search history.

(56) References Cited

U.S. PATENT DOCUMENTS 5,925,082 A   7/1999 Shimizu et al.
6,114,949 A   9/2000 Schmitz et al.
(Continued)

FOREIGN PATENT DOCUMENTS

DE    196 31 502    1/1998
DE    102004057262  6/2006
(Continued)

OTHER PUBLICATIONS

International Search Report of the International Searching Authority for International Application PCT/DE2014/200465, dated Feb. 10, 2015, 3 pages, European Patent Office, HV Rijswijk, Netherlands.
(Continued)

*Primary Examiner* — Richard Goldman
(74) *Attorney, Agent, or Firm* — W. F. Fasse

(57) ABSTRACT

A method of operating a driver assistance system of a motor vehicle for performing an automatic steering intervention involves detecting how firmly a driver is holding a steering wheel, and determining an intensity value i.e. control value dependent on how firmly the driver is holding the steering wheel. The control value is higher when the driver is holding the steering wheel more firmly, and lower when the driver is holding the steering wheel less firmly. The method then applies an automatic steering intervention with an applied intensity that is controlled in accordance with the control value, so that the applied intensity of the automatic steering intervention is higher when the driver is holding the steering wheel more firmly, and lower when the driver is holding the steering wheel less firmly. A steering assistance system
(Continued)

includes a memory, a processor, sensors and an automatic steering control system, to implement the method.

15 Claims, 2 Drawing Sheets

(51) Int. Cl.
    *B62D 6/00*     (2006.01)
    *B62D 15/02*     (2006.01)
    *B62D 5/00*     (2006.01)
    *A61B 5/00*     (2006.01)
    *A61B 5/22*     (2006.01)

(52) U.S. Cl.
    CPC .............. *B62D 5/006* (2013.01); *B62D 6/00* (2013.01); *B62D 15/025* (2013.01); *B62D 15/0265* (2013.01); *A61B 5/224* (2013.01); *A61B 2562/0247* (2013.01); *A61B 2562/04* (2013.01)

(56) References Cited

U.S. PATENT DOCUMENTS

| | | | |
|---|---|---|---|
| 7,119,672 B2 | 10/2006 | Subbaraman | |
| 8,095,271 B2 | 1/2012 | Lee | |
| 8,447,470 B2 | 5/2013 | Barthomeuf et al. | |
| 8,564,424 B2 | 10/2013 | Evarts et al. | |
| 9,159,221 B1* | 10/2015 | Stantchev | G08C 17/02 |
| 2002/0017421 A1* | 2/2002 | Stevens | B62D 5/0466 180/446 |
| 2003/0189493 A1 | 10/2003 | Klausner et al. | |
| 2005/0150711 A1* | 7/2005 | Burton | B62D 5/0466 180/443 |
| 2005/0242965 A1* | 11/2005 | Rieth | B62D 1/046 340/575 |
| 2008/0047775 A1 | 2/2008 | Yamazaki | |
| 2008/0249685 A1* | 10/2008 | Hara | B62D 5/006 701/42 |
| 2009/0024279 A1 | 1/2009 | Takeda et al. | |
| 2009/0240389 A1* | 9/2009 | Nomura | B62D 5/046 701/31.4 |
| 2010/0010712 A1* | 1/2010 | Rubia | B62D 15/025 701/42 |
| 2010/0125390 A1* | 5/2010 | Fernandez | B62D 5/0466 701/41 |
| 2011/0010054 A1* | 1/2011 | Wilson-Jones | B62D 5/0463 701/42 |
| 2011/0199200 A1 | 8/2011 | Lueke et al. | |
| 2012/0179008 A1* | 7/2012 | Burton | A61B 5/18 600/301 |
| 2012/0197493 A1* | 8/2012 | Fujimoto | B62D 15/024 701/41 |
| 2012/0296528 A1* | 11/2012 | Wellhoefer | B62D 1/046 701/48 |
| 2012/0326735 A1 | 12/2012 | Bennett et al. | |
| 2013/0079991 A1* | 3/2013 | Schmidt | B62D 6/00 701/42 |
| 2013/0151079 A1* | 6/2013 | Sworn | B62D 5/0463 701/42 |
| 2013/0211677 A1* | 8/2013 | Oblizajek | B62D 5/046 701/42 |
| 2013/0226408 A1* | 8/2013 | Fung | B60W 40/09 701/41 |
| 2014/0222295 A1* | 8/2014 | Dornhege | B62D 6/002 701/42 |
| 2015/0298726 A1* | 10/2015 | Aoki | B62D 5/0463 701/43 |
| 2015/0344068 A1* | 12/2015 | Taniguchi | B62D 15/025 701/41 |
| 2015/0379362 A1* | 12/2015 | Calmes | G06K 9/2036 348/136 |
| 2016/0031479 A1* | 2/2016 | Fung | B60W 40/09 701/42 |
| 2016/0114830 A1* | 4/2016 | Dixon | B62D 5/046 701/41 |
| 2016/0121924 A1* | 5/2016 | Norstad | B62D 5/0406 701/42 |
| 2016/0200348 A1* | 7/2016 | Lueke | B62D 1/046 701/41 |

FOREIGN PATENT DOCUMENTS

| | | |
|---|---|---|
| DE | 102007052258 | 6/2008 |
| DE | 102008002669 | 1/2010 |
| EP | 1 953 065 | 8/2008 |
| EP | 2 591 942 | 5/2013 |
| GB | 2 351 192 | 12/2000 |
| JP | 2010-023593 A | 2/2010 |
| WO | WO 2006/064343 | 6/2006 |

OTHER PUBLICATIONS

PCT International Preliminary Report on Patentability including English Translation of PCT Written Opinion of the International Searching Authority for International Application PCT/DE2014/200465, dated Apr. 5, 2016, 8 pages, International Bureau of WIPO, Geneva, Switzerland.

German Office Action in German Patent Application No. 10 2013 219 867.1, dated May 2, 2014, 5 pages, with partial English translation, 3 pages.

\* cited by examiner

METHOD AND DEVICE FOR AN AUTOMATIC STEERING INTERVENTION

FIELD OF THE INVENTION

The invention relates to the technical field of driver assistance systems, which provide an automatic steering intervention for assisting a driver.

BACKGROUND OF THE INVENTION

In the state of the art, driver assistance systems are known, e.g. systems to prevent lane departure or emergency steering systems, which provide an automatic steering intervention for assisting a driver.

Furthermore, devices are known in the state of the art, which measure a compressive force applied by the driver to the steering wheel. This can be done capacitively or with optical fibers, which have a lower light transmittance when changing a bend of the fibers. A steering wheel with an optoelectronic sensor is disclosed in the specification of the German patent DE 196 31 502 C1. The steering wheel is equipped with a fiber-optic sensor, which responds to the pressure of the hands of a driver on the steering wheel. The sensor signal varies with the amount of pressure. If e.g. a plurality of pressure sensors is applied to the steering wheel, at least one pressure sensor being arranged in the right region and one pressure sensor being arranged in the left region of the steering wheel, it can be determined whether the driver is holding the steering wheel with one or two hands. In the state of the art it is known to use a plurality of pressure sensors to evaluate, independently from one another, different pressure points on a steering wheel, e.g. the rear side on the left, on the right, or the front side, so as to reach a conclusion about a driver's intention or a driver's attention or the number of hands the driver has on the steering wheel.

Furthermore, it is known in the state of the art to deactivate a driver assistance system that influences the steering of a vehicle, wherein the deactivation is dependent on the driver's applied steering magnitude. German patent laying-open publication DE 10 2004 057 262 A1 discloses a method and a device for deactivating a driver assistance system that influences the steering of a vehicle, dependent on a driver steering magnitude, in particular if this driver steering magnitude exceeds a threshold value. This principle is known for all driver assistance systems as an overruling or overriding of the assistance system by a driver.

The driver assistance system claimed in German patent laying-open publication DE 10 2007 052 258 A1 provides that if the driver places at least one hand on the previously untouched steering wheel, the automatic lateral guidance control of the vehicle switches from the activated state to the deactivated state, and if the hand is removed from the steering wheel then the automatic lateral guidance control is reactivated.

Furthermore, it is known in the state of the art that a mechanical steering system or an electronically amplified steering system (servo steering or power steering) or an electronic steering system (Steer-by-Wire) in a vehicle converts a steering angle at the steering wheel of a vehicle into a cornering or curving path of the vehicle.

Furthermore, driver assistance systems with an automatic steering intervention such as e.g. a driver assistance system for lane keeping (Lane Keeping System) or an emergency steering system or a parking system are known or have already been implemented in today's mass-produced vehicles. The driver can recognize the automatic steering intervention by an automatic deflection of the steering wheel.

SUMMARY OF THE INVENTION

It is an object of at least some embodiments of the present invention to provide an improved method and an improved device for an automatic steering intervention, in particular for automatically controlling the intensity of an automatic steering intervention. The automatic steering intervention in the sense of the invention relates to an activated driver assistance system for an automatic steering intervention such as e.g. a driver assistance system for lane keeping or an emergency steering system or a parking system.

The background of the invention is that the result of an automatic steering intervention—namely, the actual achieved steering angle—is always connected or associated with, and subject to, a driver's manual torque that is simultaneously applied to the steering wheel. If the driver has both hands on the steering wheel, then the automatic steering intervention will have less influence on the vehicle guidance than would be the case if the driver holds only one hand loosely on the steering wheel or even is driving freehand i.e. without any hands on the steering wheel. If the driver only loosely holds the steering wheel or holds it not at all, then the effect of the automatic steering intervention will be more pronounced than if the driver holds the steering wheel firmly. Namely, when the driver holds the steering wheel only loosely or not at all, then the driver applies little or no resistance to the automatic steering intervention and thus with the same automatically applied torque the steering wheel will be rotated to a greater extent and a greater steering movement results from the larger steering angle.

It is, therefore, a central idea of at least one embodiment of the invention to provide a method for determining an intervention strength or intensity of an automatic steering intervention of a vehicle, in which the intensity is determined dependent on how solidly or firmly a driver holds the steering wheel, or dependent on how many hands the driver uses to hold the steering wheel.

Furthermore, it is a central idea of at least one embodiment of the invention that a threshold value for a maximum allowable intensity of the automatic steering intervention is determined dependent on how solidly or firmly a driver holds the steering wheel or dependent on how many hands the driver uses to hold the steering wheel. In such an embodiment of the invention, the idea of security or safety is predominant. By the given dependence of the threshold value it can be ensured that the vehicle remains controllable by the driver during the autonomous steering operation. This applies in particular for an embodiment of the invention, in which the threshold value is increased with an increasing compressive force applied by the driver to the steering wheel or with an increasing number of hands on the steering wheel.

The effectiveness of the automatic steering intervention is thus estimated in advance, and is taken into account in the selected intensity or it is ensured that the vehicle remains controllable by the driver even during the autonomous steering movement.

BRIEF DESCRIPTION OF THE DRAWINGS

In order that the invention may be clearly understood, it will now be explained in further detail in connection with example embodiments thereof, with reference to the accompanying drawings, wherein.

DETAILED DESCRIPTION OF THE PREFERRED EMBODIMENTS

Figure 1:
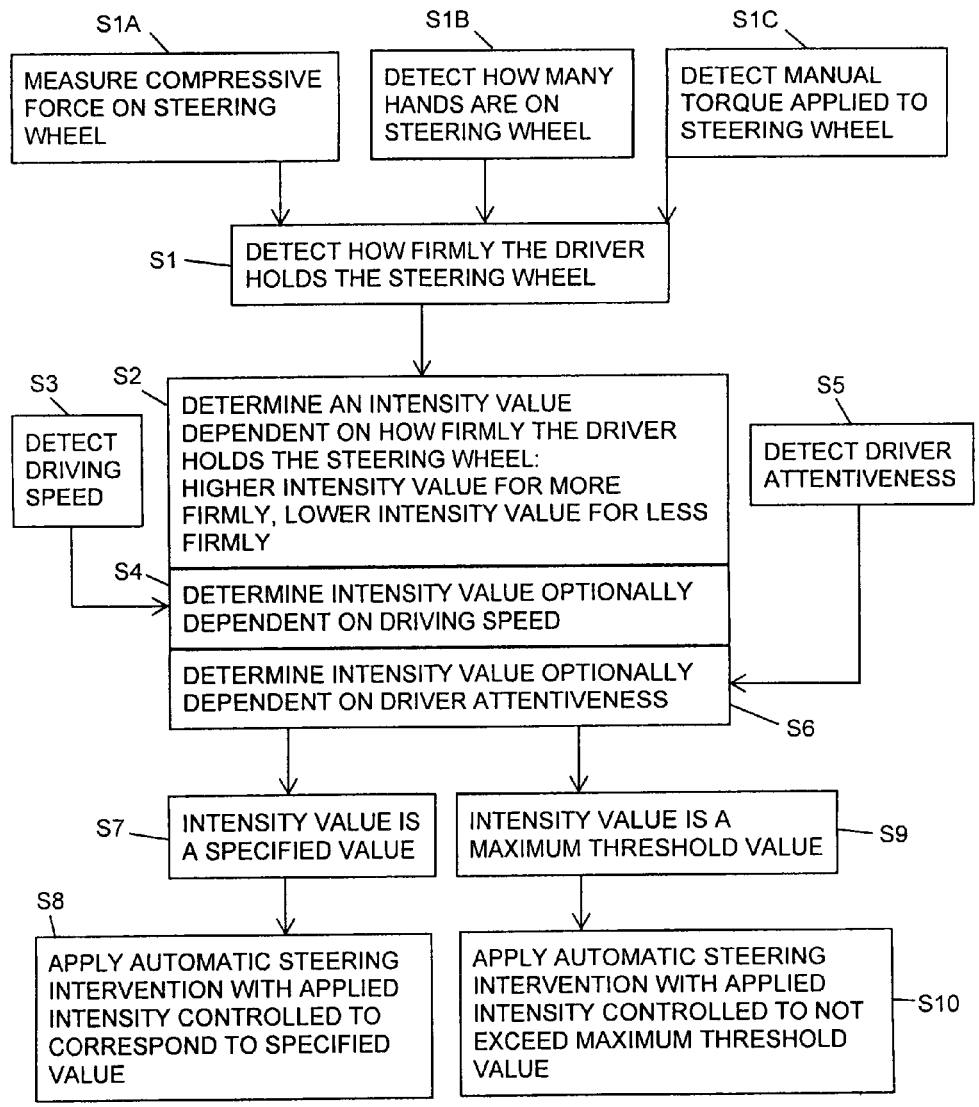
FIG. 1 is a flow diagram representing steps and features of several embodiments of a method according to the invention.

FIG. 1 diagrammatically represents steps and features of several embodiments of a method according to the invention. The method according to the illustrated embodiment(s) generally begins with a step S1 of detecting how firmly the driver of the motor vehicle is holding the steering wheel. This can be detected by measuring the compressive force applied by the driver's hands on the steering wheel in a step S1A, by detecting how many hands of the driver (zero, one or two) are holding the steering wheel in a step S1B, and/or detecting the manual torque applied by the driver to the steering wheel in a step S1C.

Next, in step S2 the method proceeds with determining an intensity value i.e. a control value dependent on how firmly the driver is holding the steering wheel, with a higher intensity value (control value) when the driver holds the steering wheel more firmly, and a lower intensity value (control value) when the driver holds the steering wheel less firmly. Optionally, in a further embodiment, the inventive method involves detecting the driving speed in a step S3 and determining the intensity value (control value) further dependent on the driving speed in a step S4. Another optional embodiment involves detecting the driver attentiveness in a step S5, and determining the intensity value (control value) further dependent on the driver attentiveness in a step S6.

In one embodiment, the intensity value (control value) is a specified value of intensity at which the automatic steering intervention shall be applied, according to a step S7, and then a step S8 involves applying the automatic steering intervention with the applied intensity thereof controlled to correspond to the specified value. In another embodiment according to step S9, the intensity value (control value) is a maximum threshold value which the applied intensity of the automatic steering intervention shall not exceed according to step S9, and the method then proceeds with a step S10 of applying the automatic steering intervention with the applied intensity thereof controlled not to exceed the maximum threshold value.

In a particular embodiment of the invention, the intensity value (control value) is additionally increased, if required by the environmental situation as detected by an environment sensor system 9 (see FIG. 2) and if the driver holds the steering wheel 3 solidly and/or with two hands, so that even with an increased intensity value (control value he could overrule or override the assistance system 2 with a high probability.

In a preferred embodiment of the invention, the intensity value (control value) is determined in accordance with a driver manual torque (step S1C) or a compressive force (step S1A) applied by the driver to the steering wheel 3. The compressive force applied to the steering wheel 3 suggests the number of hands on the wheel, in particular if a plurality of pressure sensors e.g. first sensors 6 is provided at different places on the steering wheel 3.

Furthermore, on the basis of pressure sensors, a conclusion can be reached about the intensity or firmness of the grip of the one or two hands of the driver with the steering wheel 3. From this in turn it can be derived how strongly an automatic intervention would be damped by the driver or with what reaction force the driver could override an automatic intervention.

In a preferred embodiment of the invention the intensity value (control value) increases with an increasing driver manual torque (step S1C).

With an increasing compressive force applied by the driver to the steering wheel (step S1A) or with an increasing number of hands on the steering wheel (step S1B), the intensity value (control value) is increased, as a stronger damping by the driver can be expected.

In a further embodiment of the invention according to steps S9 and S10, a maximum allowable intensity value (control value is limited by an upper threshold value. This threshold value is chosen in accordance with how solidly or firmly a driver holds the steering wheel or with how many hands the steering wheel is held. If the steering wheel is held increasingly firmly, in particular with an increasing compressive force applied by the driver to the steering wheel (step S1A) or with an increasing number of hands on the steering wheel (step S1B), then the threshold value is increased.

In a preferred embodiment of the invention, the intensity of the automatic steering intervention is varied by changing a magnitude of a torque applied to the steering wheel and/or a duration of a torque applied to the steering wheel. The intensity of the intervention is increased by increasing the torque and/or the duration of the torque.

Figure 2:
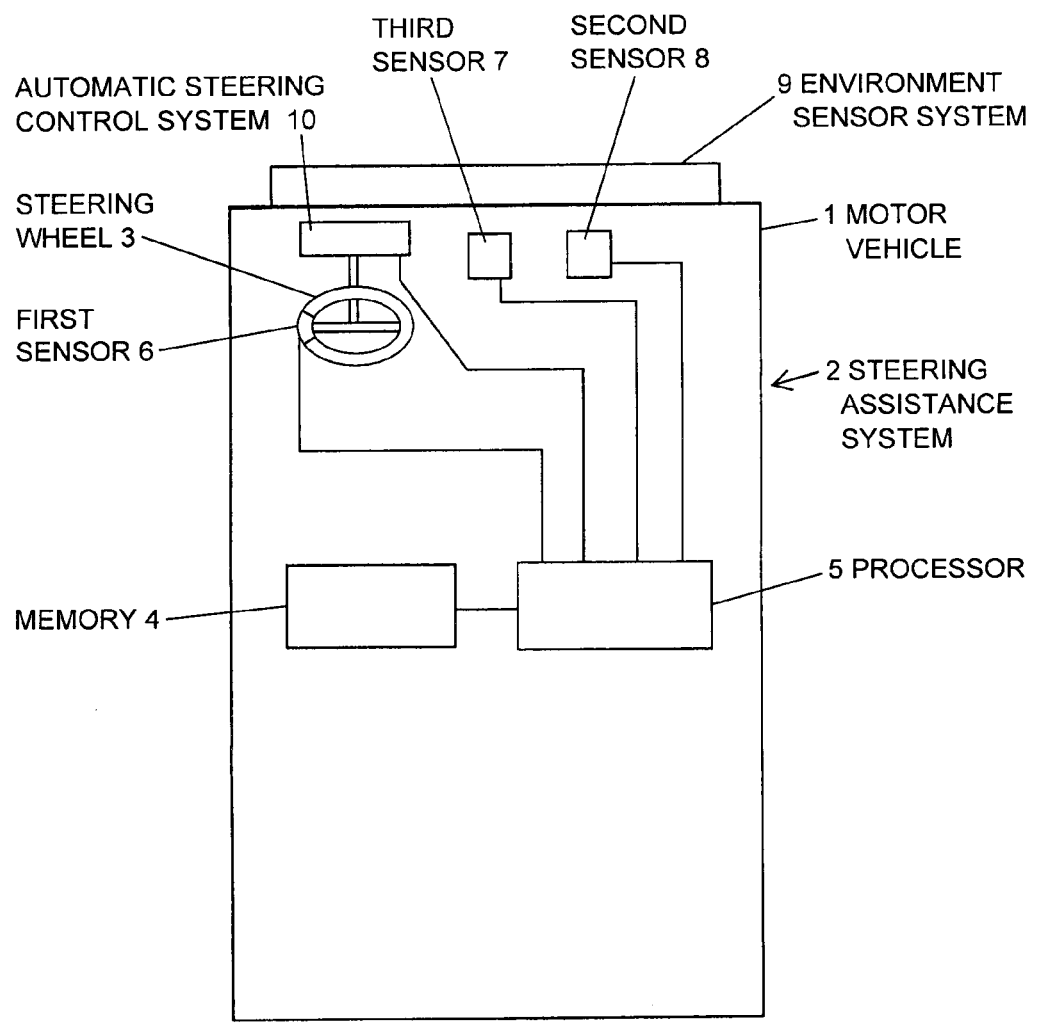
FIG. 2 is a schematic diagram of a steering assistance system according to an embodiment of the invention incorporated in a motor vehicle.

In a particular embodiment according to steps S3 and S4, the intensity value (control value) is determined further dependent on a speed of the vehicle as detected by a second sensor 8 (see FIG. 2). With an increasing vehicle speed, the intensity value (control value) decreases, in particular because the automatic intervention, but also especially any incorrect intervention, more strongly affects the driving behavior and the driving situation.

In a further embodiment of the invention, the intensity value (control value) is also determined in accordance with a driver attention detection using a third sensor 7 (see FIG. 2) according to steps S5 and S6 (see FIG. 1). The driver attention can be detected with the third sensor 7, e.g. with an interior camera that records the driver's viewing direction. Alternatively, the driver activity can be assessed using another suitable third sensor, e.g. if the driver actuates the gas or brake pedal or the steering wheel, it can be concluded that the driver is attentive. If the driver is now aware and paying attention, and has two hands on the steering wheel and/or holds the steering wheel firmly in his hands, then a higher intensity value (control value) can be chosen than if the driver was inattentive.

As schematically shown in FIG. 2, an embodiment of the invention also provides a device or steering assistance system 2 for an automatic steering intervention, which is provided in a motor vehicle 1 and comprises a sensor system 9 for detecting an environmental situation. With the sensor system 9, the necessity of an automatic steering intervention is detected, e.g. if the vehicle departs from its proper lane or will be doing so shortly. Similarly, an automatic steering intervention can be carried out in case of a risk of collision in order to evade a potential collision object.

Moreover, the device or system 2 further comprises a memory 4 on which a program for carrying out a method as described above is stored, and a processor 5 for performing the method by executing the program. Furthermore, a device or automatic steering control system 10 is provided for outputting a torque to a steering wheel 3 of the vehicle 1, wherein the strength i.e. magnitude and/or the time duration of the torque is controlled dependent on the determined intensity value (control value) for the automatic steering intervention.

The invention claimed is:

1. A method of operating a driver assistance system of a motor vehicle for performing an automatic steering intervention, comprising the steps:
    a) with at least one first sensor of the driver assistance system, detecting how firmly a driver of the motor vehicle is holding a steering wheel of the motor vehicle, and producing a corresponding first output that is indicative of how firmly the driver is holding the steering wheel;
    b) with a processor of the driver assistance system, determining a control value dependent on the first output; and
    c) with a torque output device of the driver assistance system, applying an automatic steering intervention to a steering system of the motor vehicle, wherein an applied intensity of the applied automatic steering intervention is controlled in accordance with the control value so that the applied intensity of the applied automatic steering intervention is higher when the driver is holding the steering wheel more firmly and lower when the driver is holding the steering wheel less firmly.

2. The method according to claim 1, wherein the detecting in the step a) comprises detecting how much compressive force the driver is applying onto the steering wheel with one or two hands of the driver, wherein a higher compressive force indicates that the driver is holding the steering wheel more firmly and a lower compressive force indicates that the driver is holding the steering wheel less firmly.

3. The method according to claim 1, wherein the detecting in the step a) comprises detecting how many hands of the driver is or are holding the steering wheel, wherein a higher number of hands indicates that the driver is holding the steering wheel more firmly and a lower number of hands indicates that the driver is holding the steering wheel less firmly.

4. The method according to claim 1, wherein the detecting in the step a) comprises detecting a manual torque applied by the driver to the steering wheel, wherein a higher manual torque indicates that the driver is holding the steering wheel more firmly and a lower manual torque indicates that the driver is holding the steering wheel less firmly.

5. The method according to claim 1, wherein the control value determined in the step b) is a specified value of intensity with which the automatic steering intervention shall be applied, and in the step c) the applied intensity of the applied automatic steering intervention is controlled to correspond to the control value.

6. The method according to claim 1, wherein the control value determined in the step b) is a threshold value for a maximum allowable intensity which the applied intensity of the automatic steering intervention shall not exceed, and in the step c) the applied intensity of the applied automatic steering intervention is controlled to not exceed the control value.

7. The method according to claim 1, further comprising with a second sensor detecting a driving speed of the motor vehicle and producing a corresponding second output that is indicative of the driving speed, and wherein in the step b) the control value is determined further dependent on the second output.

8. The method according to claim 1, further comprising with a third sensor detecting an attentiveness of the driver and producing a corresponding third output that is indicative of the attentiveness of the driver, and wherein in the step b) the control value is determined further dependent on the third output.

9. The method according to claim 1,
    wherein the driver assistance system is a system selected from a group consisting of an automatic steering assistance system, an emergency steering assistance system and a lane keeping system of the motor vehicle,
    wherein the selected system includes comprises an environment sensor system, and
    wherein the automatic steering intervention is applied in response to and dependent on an output of the environment sensor system.

10. The method according to claim 1, wherein in the step c) the applying of the automatic steering intervention comprises automatically applying a steering torque, and the applied intensity comprises a torque magnitude of the applied steering torque.

11. The method according to claim 1, wherein in the step c) the applying of the automatic steering intervention comprises automatically applying a steering torque, and the applied intensity comprises a time duration of the applied steering torque.

12. The method according to claim 1, wherein the control value is set to a level whereby the applied intensity of the applied automatic steering intervention is below an intensity of a manual control that can be applied manually by the driver to the steering wheel with the present firmness of holding the steering wheel, so that the driver's manual control can override the automatic steering intervention.

13. A driver assistance system for performing the method according to claim 1, comprising:
    an environment sensor system for detecting an environmental situation outside the motor vehicle,
    the at least one first sensor,
    a memory on which a program for performing the method is stored,
    the processor for executing the program, and
    the torque output device for applying the automatic steering intervention to the steering system of the motor vehicle.

14. The method according to claim 7, wherein the control value is determined dependent on the second output so that the applied intensity of the automatic steering intervention decreases as the driving speed increases.

15. The method according to claim 1, further comprising determining a resultant steering angle to be achieved by the automatic steering intervention, and wherein the applied intensity of the automatic steering intervention is controlled so as to overcome a resistance imposed by the driver holding the steering wheel so as to achieve the determined resultant steering angle whether the driver is holding the steering wheel more firmly or less firmly.

* * * * *